United States Patent [19]

Goldberg et al.

[11] 4,351,341
[45] Sep. 28, 1982

[54] BALLOON CATHETER

[75] Inventors: Edward M. Goldberg, Glencoe; Seymour Bazell, Skokie, both of Ill.

[73] Assignee: UreSil Company, Morton Grove, Ill.

[21] Appl. No.: 178,305

[22] Filed: Aug. 15, 1980

[51] Int. Cl.³ ............................................. A61M 25/00
[52] U.S. Cl. .................................... 128/348; 128/774
[58] Field of Search ............... 128/774, 778, 780, 325, 128/344, 348–350

[56] References Cited

U.S. PATENT DOCUMENTS

| | | | |
|---|---|---|---|
| 2,892,458 | 6/1959 | Auzin | 128/349 B |
| 3,044,468 | 7/1962 | Birtwell | 128/349 B |
| 3,467,101 | 9/1969 | Fogarty et al. | 128/348 |
| 3,794,036 | 2/1974 | Carroll | 128/207.15 |
| 3,924,634 | 12/1975 | Taylor et al. | 128/349 B |
| 4,044,765 | 8/1977 | Kline | 128/348 X |
| 4,133,303 | 1/1979 | Patel | 128/780 |
| 4,149,539 | 4/1979 | Cianci | 128/325 |
| 4,263,917 | 4/1981 | Moss | 128/656 |

Primary Examiner—Dalton L. Truluck
Attorney, Agent, or Firm—Hume, Clement, Brinks, Willian & Olds, Ltd.

[57] ABSTRACT

A balloon catheter for insertion in a body passage includes an elongated coil spring which defines a lumen. This coil spring is covered by a silicone covering which includes an extensible sheath, a strain relief collar affixed to the sheath, and a balloon tip affixed to the strain relief collar. The extensible sheath and a portion of the elongated coil spring form in combination a support structure which perceptibly elongates when an excessive stretching force is applied to the support structure in pulling the balloon through a body passage. As this support structure elongates, the volume of the lumen of the coil spring increases. Preferably the balloon is in fluid communication with the lumen of the coil spring such that the volume of the balloon is reduced when the support structure elongates. The strain relief collar is adapted to extend away from the spring to receive fluid from the balloon to reduce fluid pressure within the balloon when fluid pressure within the balloon exceeds a predetermined value. One preferred embodiment includes a flexible disc-shaped chamber in fluid communication with the balloon, which chamber is sized to fit between the thumb and opposing finger of a user.

25 Claims, 9 Drawing Figures

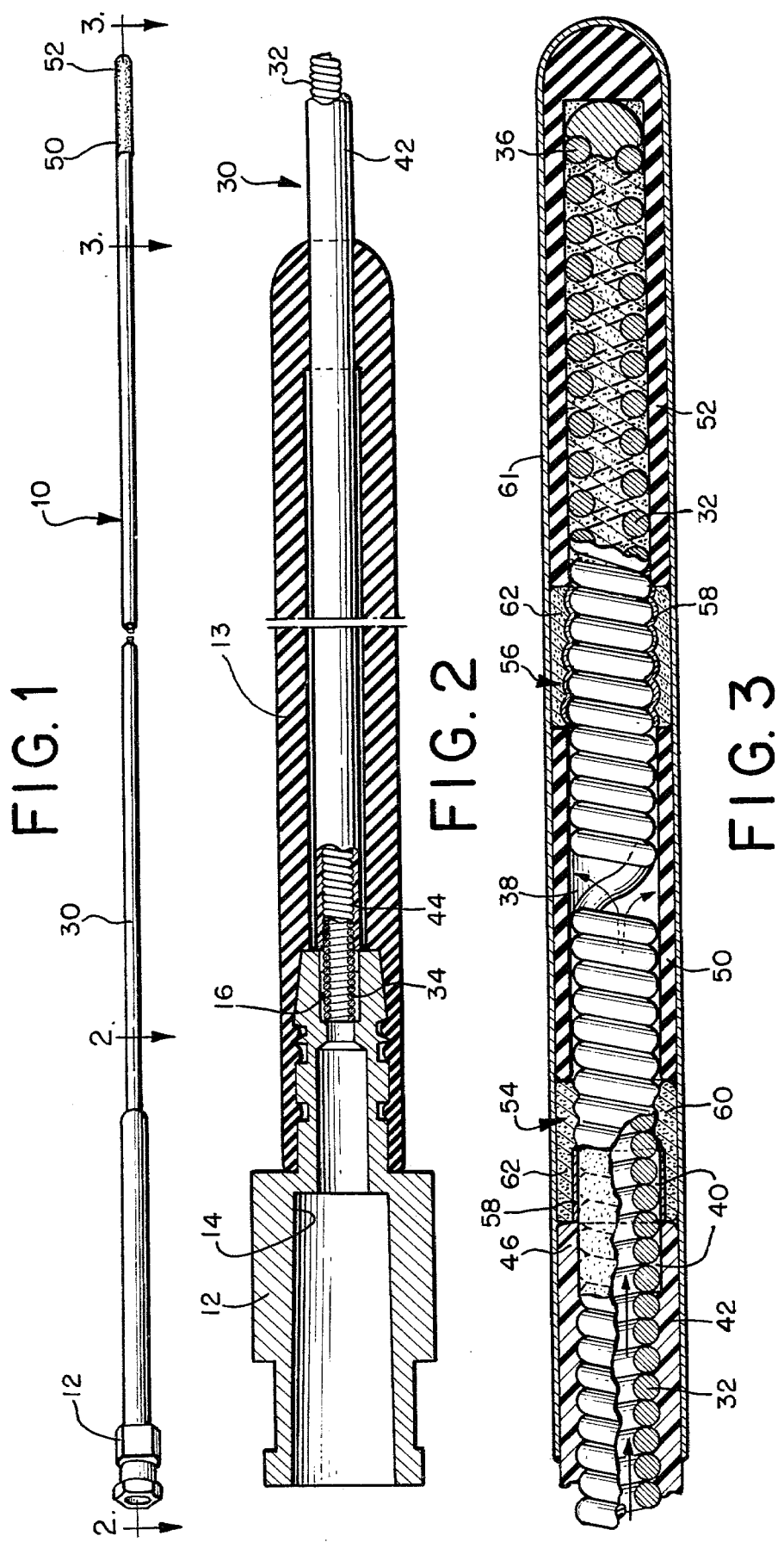

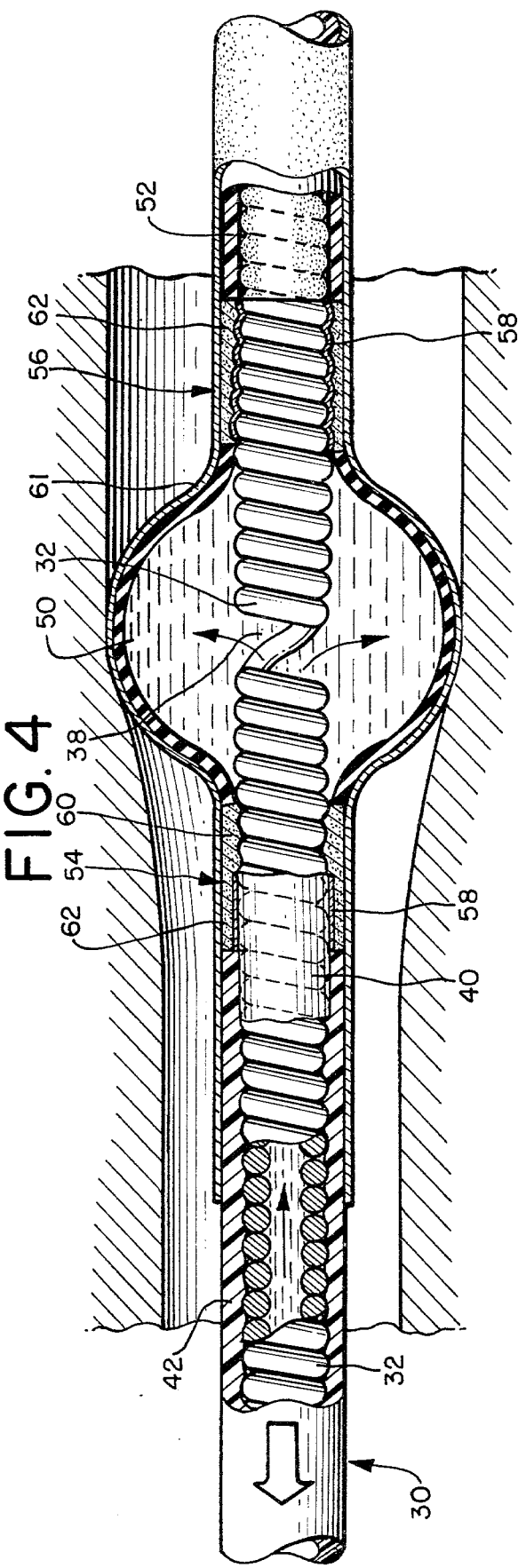
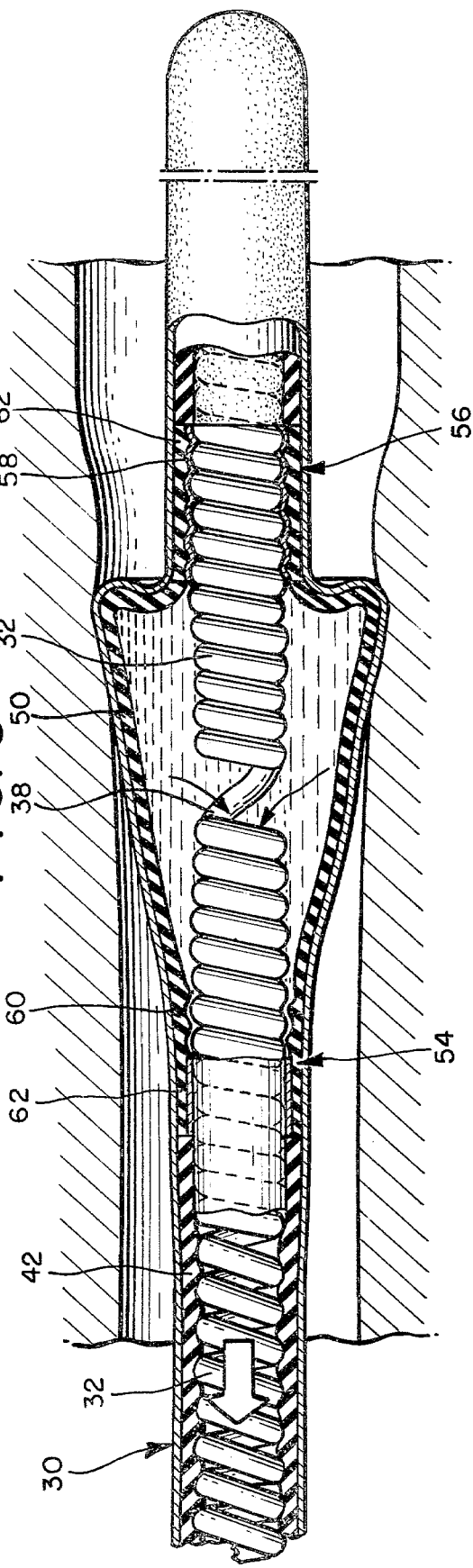

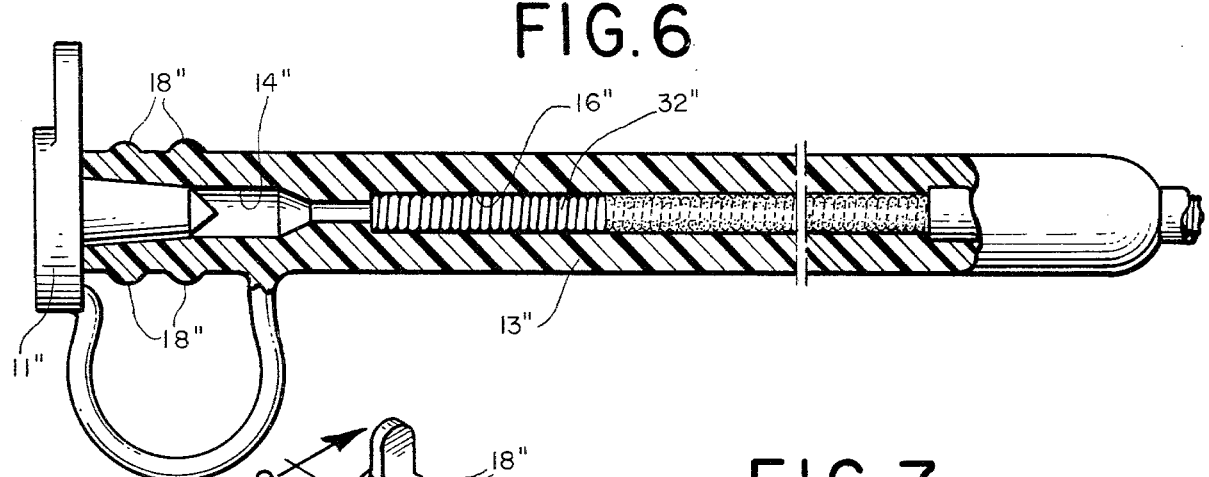
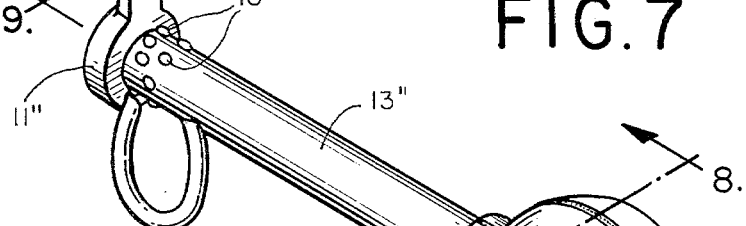
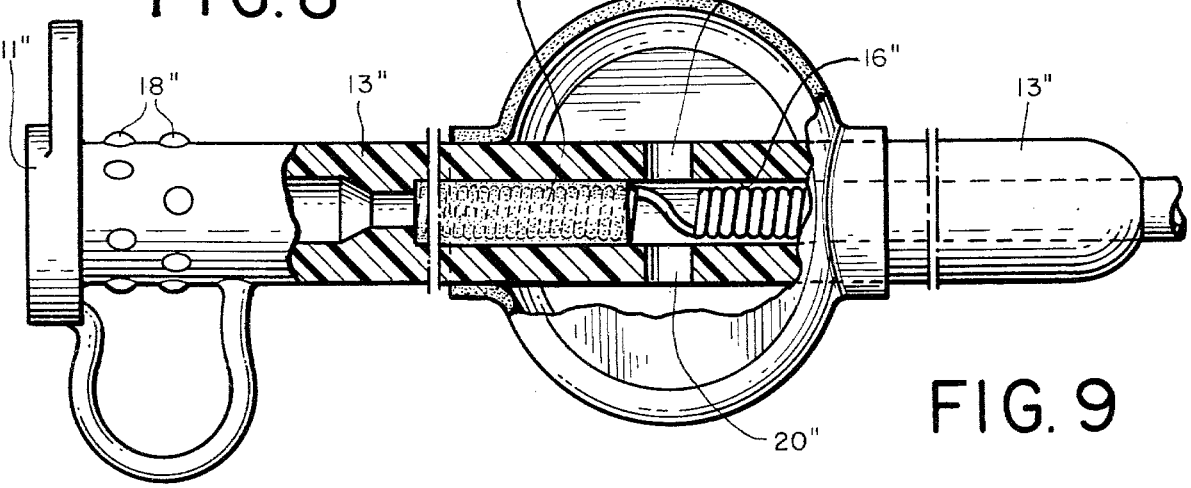

BALLOON CATHETER

BACKGROUND OF THE INVENTION

The present invention relates to an improved balloon catheter for insertion in a body passage.

Balloon catheters of various types are known to the art. For example, U.S. Pat. No. 3,435,826 (Fogarty) and U.S. Pat. No. 3,467,101 (Fogarty, et al.) disclose two types of embolectomy catheters used to remove blood clots from blood vessels. As explained in the earlier Fogarty patent, such a catheter is used by first inserting it through an incision into a blood vessel and moving the deflated balloon to a point beyond the clot, then inflating the balloon on the remote side of the clot and withdrawing the catheter. The balloon acts as a drag to push the clot ahead of it until it reaches the incision where it can be readily withdrawn.

The use of such balloon catheters brings with it certain dangers. If excessive transmitted wall pressures and excessive shear stresses are applied to the vessel wall in withdrawing the catheter from the blood vessel, the blood vessel can be seriously damaged or even ruptured. Furthermore, if the balloon or other parts of the catheter fragment while in use, portions of the catheter can become lost in the vessel, thereby creating the danger of obstructions in the vascular system.

SUMMARY OF THE INVENTION

The present invention is directed to an improved balloon catheter which provides important safety advantages over catheters of the prior art.

According to one aspect of this invention, a catheter includes a balloon mounted on an elongated support structure which is elongatable in response to an applied stretching force greater than a first value. This first value is chosen such that the support structure elongates perceptibly when an excessive stretching force is applied to the support structure in pulling the balloon through a body passage, thereby providing a tactile indication to a user of the catheter that an excessive stretching force is being applied.

Preferably, the support structure includes a coil spring covered with an extensible sheath, and the coil spring is tightly wound with adjacent coils in contact with each other such that elongation of the support structure is imperceptible for stretching forces smaller than a threshold value, less than or equal to the first value. However, when stretching forces greater than the first value are applied, the support structure elongates perceptibly. By setting the first value at a point greater than that needed to pull the balloon safely through the body passage but less than that at which damage is done to the body passage, the user of the catheter is given a tactile signal whenever he applies an excessive stretching force to the catheter. In addition, the support structure is preferably constructed to temporarily receive fluid and relieve pressure from the balloon when the support structure elongates. This reduces balloon volume and pressure, thereby further reducing the danger of damaging the body passage in the event an excessive stretching force is applied to the catheter.

According to a second aspect of the invention, a balloon catheter is provided with a balloon and means for receiving and storing fluid from the balloon to temporarily reduce the volume of the balloon when the fluid pressure in the balloon exceeds a predetermined value. In this way strain on the balloon, as well as the pressure exerted by the balloon on the body passage, are automatically reduced when excessive pressures are created in pulling the balloon through a body passage.

Preferably, the receiving means includes a strain relief collar mounted adjacent the balloon. This relief collar moves into an extended position in response to excessive fluid pressure or tension on the balloon to receive fluid from the balloon. Furthermore, the preferred relief collar provides further advantages in terms of improved reliability of the bond between the balloon and the catheter.

According to a third aspect of the invention, a balloon catheter is provided with a chamber in fluid communication with the balloon, which chamber is provided with at least one flexible, deformable wall. This chamber is adapted to be manipulated by digital pressure of a user to provide precise and direct control of the inflation pressure of the balloon. Preferably, the chamber includes an elastomeric chamber included as an integral part of the balloon catheter and sized to fit between the thumb and an opposed finger of the user such that the thumb of the user bears directly on the deformable wall of the chamber.

According to a fourth aspect of the invention, the balloon and the outer layer of the support structure are formed of silicone rubber, which has a reduced tendency to fragment if it ruptures. Furthermore, silicone rubber is extensible, it does not soften excessively at body temperature, and it provides a balloon which conforms readily to the contours of the body passage. If excessive stretching forces are applied in withdrawing the silicone rubber balloon, it tends to extend longitudinally in a pear shaped configuration, further limiting shear stress and the concomitant danger of vessel damage. Preferably, the balloon is directly bonded to the catheter rather than being held by means of ties, because ties and the balloon can become lost in the body passage if they separate from the catheter in use.

The invention, together with further objects and attendant advantages, will be best understood by reference to the following detailed description taken in conjunction with the accompanying drawings.

BRIEF DESCRIPTION OF THE DRAWINGS

FIG. 1 is a perspective view of a first preferred embodiment of the balloon catheter of this invention.

FIG. 2 is a cross-sectional view of the luer portion of the balloon catheter of FIG. 1 taken along line 2—2 of FIG. 1.

FIG. 3 is a cross-sectional view of the tip portion of the balloon catheter of FIG. 1 taken along line 3—3 of FIG. 1, showing the balloon in its deflated state.

FIG. 4 is a cross-sectional view of the tip portion of the balloon catheter of FIG. 1, showing the balloon in its inflated state.

FIG. 5 is a cross-sectional view of the tip portion of the balloon catheter of FIG. 1, showing the balloon inflated, elongated and pear shaped as it is pulled through a body passage.

FIG. 6 is a partial sectional view of a second preferred embodiment showing an alternate construction for the proximal portion of the catheter of this invention.

FIG. 7 is a perspective view of the proximal end of a third preferred embodiment of the catheter of this invention.

FIG. 8 is a sectional view taken along line 8—8 of FIG. 7.

FIG. 9 is a sectional view taken along line 9—9 of FIG. 8.

DETAILED DESCRIPTION OF A PREFERRED EMBODIMENT

Referring now to the drawings, FIG. 1 provides an overall view of a first preferred embodiment of the balloon catheter of this invention, which is indicated generally by the reference numeral 10. This catheter 10 is made up of three major components: a luer 12, a support structure 30, and a balloon tip assembly 50,52. Each of these major components will be described in detail.

As shown in FIG. 2, the luer 12 is a conventional syringe luer used to couple the balloon catheter 10 to a syringe (not shown) used to inflate the balloon 50. In this embodiment, the luer 12 is a metal adaptor No. 3084 L/609, marketed by Becton, Dickinson & Co. of Rutherford, N.J. This luer 12 includes a syringe receiving bore 14 sized to securely attach to the projecting end of a syringe, and a spring receiving bore 16. The spring receiving bore 16 is preferably swaged to achieve an internal diameter of 0.039 inches.

The support structure 30 includes an internal coil spring 32 and an external sheath 42. The coil spring 32 includes a proximal end 34 which is inserted in the spring receiving bore 16 of the luer 12 and is soldered, swaged or screwed in place so as to securely attach the coil spring 32 to the luer 12. A support tube 13 of silicone rubber surrounds a portion of the luer 12 and the adjacent portion of the support structure. Furthermore, the coil spring 32 defines a distal end 36 which is soldered or welded to form a rounded end, as shown in FIG. 3. Preferably, the coil spring 32 has an outer diameter of 0.040 inches and is formed from closely spaced coils of stainless steel type 304, and is made of wire having a cross-sectional diameter of 0.011 inches. Throughout the length of the coil spring 32, the coils are in close contact with one another, except that at one point approximately 23/64 of an inch from the distal end 36, where the coils are spread as shown at reference numeral 38 of FIG. 3 and at the distal end of the spring 32. In addition, a number of coils of the spring 32 spread over a distance of about ⅛ inch are bonded together with a solder bond 40, also as shown in FIG. 3.

The coil spring 32 is covered with a elongatable sheath 42 in the region between the luer 12 and the solder bond 40. Preferably, this sheath is formed of silicone rubber tubing having an outside diameter (before it is assembled with the coil spring 32) of 0.052 inches. In this preferred embodiment the wall thickness of the sheath 42 is 0.013 inches, and the wall thickness is uniform to within one-thousandth of an inch. Preferably, insertion depth gauge marks at ten centimeter intervals are applied to the sheath 42. The sheath 42 is placed on the coil spring 32 by first expanding the silicone rubber of the sheath 42 with toluene. After the sheath 42 has been expanded it is then placed over the spring 32 and is then allowed to dry and shrink in place on the spring 32. The sheath 42 includes a proximal end 44 adjacent the luer 12 and a distal end 46 adjacent the balloon 50.

The distal end 36 of the spring 32 is covered with a balloon 50 and a tip section 52. Preferably the balloon 50 is bonded directly to the distal end 46 of the sheath 42 in a bonding region 54, and the tip section 52 is bonded directly to the balloon 50 in a bonding region 56. The structure of these bonding regions 54, 56 will be discussed in detail below. The tip section 52 is bonded to the spring 32 by means of a silicone rubber adhesive which fills the lumen of the spring 32 and all other space within the tip section 52. Preferably the tip section 52 is molded to a predetermined shape. This molding provides uniformity of size and wall thickness of the tip section 52, and allows the tip section to be pre-formed into the desired shape.

Preferably, the balloon 50 is approximately 5/32 of an inch in length, is formed of silicone rubber, and has a rest state diameter prior to assembly of 0.052 inches. The wall thickness of the balloon 50 is 0.010 inches, and the wall thickness is uniform to within 5/10,000 of an inch or less. The tip section 52 is also formed of silicone rubber in this preferred embodiment. The length of the tip section is about one quarter of an inch in length, and it has a rest diameter (prior to assembly) of 0.050 inches. The wall thickness of the tip section is preferably 0.005 inches. When assembled, the balloon 50 is centered on the spread section 38 of the coil spring 32.

The bonding regions 54 and 56 as shown in FIGS. 3–5, are each about 1/16 of an inch in length in this preferred embodiment. The bonding region 54 includes a strain relief collar 60 adjacent the balloon 50, and a secured section 62 adjacent the sheath 42. A coating of a primer 58 is applied between the secured section 62 and the coil spring 32 in order to insure that the secured section 62 adheres firmly to the coil spring 32. Both the strain relief collar 60 and the secured section 62 are formed from silicone rubber adhesive in this preferred embodiment. In addition, the bonding region 56 is also preferably formed of silicone rubber applied over a coating of a primer 58 to bond the bonding region 56 to the spring 32. Thus, in this preferred embodiment, the sheath 42, the bonding regions 54,56, the balloon 50, and the tip section 52 are all formed of silicone rubber. Preferably, the bonding regions 54,56 are bonded to the silicone rubber sheath 42, balloon 50 and tip section 52 in order to securely bind each of the component parts of the balloon catheter into a single unit. In this way, the use of windings is avoided and an integral balloon catheter is provided. After the balloon catheter 10 is fully assembled, the distal end of the catheter 10 is dip coated with two coats of silicone rubber 61. This dip coating covers the distal ¾ of an inch of the catheter.

The dimensions of the preferred embodiment described above are appropriate for a size 4 (French) catheter. Of course, it should be understood that these dimensions are merely illustrative, and are not to be taken as limiting the scope of the invention, which is suitable for use in a wide range of catheter sizes. For example, the present invention can be embodied in catheters ranging as small as size 2 (French) or even smaller, and as large as size 7 (French), or even larger. The dimensions described above can be appropriately scaled for a wide range of catheter sizes.

In this preferred embodiment, the support tube 13, the sheath 42, the balloon 50 and the tip section 52 are all formed of food grade silicone rubbers having the desired durometers and extensibility. Silicone rubbers marketed by Dow Corning, General Electric and Stauffer-Waker-Stauffer are blended to produce compounds with the desired physical characteristics. The primer 58 is preferably primer No. 608 marketed by Hughson Chemical Division of Lord Chemical Corp. The adhesive used to secure the tip section 52 to the spring 32 and to form the bonding regions 54 is preferably adhesive No. 951 marketed by Stauffer-Waker-Stauffer. In addition, the spring 32 is preferably chosen such that the support structure does not elongate for stretching forces less than about one-half pound, and that the entire catheter elongates at a rate of about one inch for each one-half pound of force in excess of one-half pound.

FIG. 6 shows a portion of a second preferred embodiment of the catheter of this invention. This second preferred embodiment is identical to the embodiment of FIG. 1 except for the portion shown in FIG. 6, which includes a modified support tube 13". This support tube 13" is preferably formed of an elastomeric material such as silicone rubber, and it defines a spring receiving bore 16" and a syringe receiving bore 14". The syringe receiving bore 14" is sized to receive the projecting end of a syringe, and a cap 11" is molded to the tube 13" for sealing the bore 14" during storage. Preferably, a plurality of raised bumps 18" are molded in the tube 13" to engage the projecting end of a syringe (not shown). Helical or circumferential ridges could be substituted for the bumps 18". The spring 32" is securely bonded to the tube 13" in the spring receiving bore 16" by means of a suitable adhesive or the like.

This second preferred embodiment eliminates the need for metal luers such as the luer 12 of FIG. 2. In some applications, this may reduce manufacturing costs.

FIGS. 7, 8 and 9 show a portion of a third preferred embodiment of the invention. This third preferred embodiment is identical to that of FIG. 6 with the following exceptions. The tube 13" includes a pair of opposed openings 20" which extend from the outside of the tube 13" to the interior of the spring receiving bore 16". The spring 32" is provided with a spread portion 22" adjacent these opening 20" to allow fluid to flow from the openings 20" into the lumen of the spring 32". A chamber 24" is disposed around the tube 13" adjacent the openings 20". Preferably, this chamber 24" is formed of two symmetrical halves 26", 28" which are bonded to each other and to the tube 13" such that the chamber 24" is fluid tight and fluid can only enter or escape from the chamber 24" via the openings 20". Preferably the chamber 24" is formed of flexible material which has a low extensibility, such that pressure variations of the fluid within the chamber 24" can readily be sensed by finger pressure on the outer walls of the chamber 24". Preferably the chamber 24" is made of silicone rubber having a durometer in the range of 50-75.

The chamber 24" should have a rest state which defines a volume adequate to receive enough fluid from the balloon to totally deflate the balloon. This volume should be large enough that finger pressure on the chamber 24" can be used to inflate the balloon to the maximum extent necessary.

Having described the structure of the presently preferred embodiments, the various safety features of the balloon catheter of this invention can now be described. As shown in FIG. 4, when the balloon catheter 10 is normally inflated, the balloon 50 is pushed away from the spring 32 by fluid which passes through the lumen of the coil spring 32 out the spread section 38 into the interior of the balloon 50. Normally, both the strain relief collar 60 and the secured section 62 of the bonding region 54, as well as the bonding region 56, remain against the spring 32. Once the balloon 50 has been inflated as shown in FIG. 4, it is then pulled through a body passage to remove material such as blood clots.

FIG. 5 shows a configuration of the balloon catheter 10 when excessive fluid pressure and over distension is developed within the balloon 50. Typically, this occurs when pulling forces are applied to the catheter in drawing the balloon 50 through a body passage. Under these conditions the balloon 50, when pulled, tends to elongate to form a pear shape and to pull back towards the distal end of the spring 32. Because the balloon 50 is formed of silicone rubber it is capable of elongating in this way in order to reduce the contact area between the balloon 50 and the inner walls of the body passage and therefore the total applied force. When the strain on the balloon 50 and the fluid pressure within the balloon 50 become excessive, the bonding region 54 is designed such that the strain relief collar 60 extends away from the coil spring 32. This extension provides two important safety advantages. First, when the collar 60 extends it effectively increases the volume of the balloon 50, because it temporarily receives and stores a portion of the fluid contained in the balloon 50. This of course tends to reduce the pressure applied to the body passage. In addition, when the strain relief collar 60 extends as shown in FIG. 5, it in effect lengthens the balloon 50 and reduces the strain placed on the bond between the proximal end of the balloon 50 and the strain relief collar 60 as well as the strain on the balloon 50. By relieving strain in this area, the life of the bond between the strain relief collar and the balloon 50 as well as the life of the balloon are increased. Thus, the strain relief collar 60 serves both to reduce pressure on the body passage under conditions of unusually high fluid pressure and to extend the life of the balloon 50.

FIGS. 4 and 5 illustrate a second important safety feature of the balloon catheter 10. As previously mentioned, the support structure 30, which in this preferred embodiment is about 35 inches long, includes a coil spring 32 and a sheath 42. In its rest state, as shown in FIG. 4, the coil spring 32 is a closely wound spring in which adjacent coils are in contact. However, both the spring 32 and the sheath 42 are extendable when sufficient stretching force is applied to the catheter. FIG. 5 shows a configuration of the support structure 30 when an excessive stretching force is applied, thereby causing adjacent coils of the coil spring 32 to separate. The spring 32 is preferably chosen such that for stretching forces below a threshold value the coils of the spring 32 remain adjacent one another. Thus, when a user exerts light or moderate pulling force in withdrawing the inflated balloon through a body passage, the support structure 32 remains substantially inextensible. Any minor extension of the support structure 30 is imperceptible to the physician, and the support structure 30 appears to have a fixed length.

However, when excessive stretching forces are applied, the coils of the spring 32 will spread as shown in FIG. 5. This extension of the support structure 30 provides several important advantages. First, it provides a tactile signal to the user that an excessive stretching force is being applied. This provides an immediate indication to the user that the stretching force and/or balloon distension should be reduced in order to prevent damage to the body passage. Second, the elongation of the support structure 30 tends to reduce the stretching force applied to the balloon 50 as it is being withdrawn from the body passage. Third, when the support structure 30 elongates, the volume of the support structure 30 increases. In this embodiment, this is because the coil spring 32 prevents the sheath 42 from reducing its internal diameter substantially as the coil spring 32 elongates. This increase in internal volume of the support structure 30 tends to decrease the volume of the balloon 50 when an excessive stretching force is applied to the luer 12. Thus, the support structure 30 of this preferred embodiment simultaneously removes fluid from the balloon to reduce balloon pressure, and provides tactile feedback to the physician when an excessive stretching force is applied. In this way, the danger of rupturing the body passage or of producing severe intimal damage to the body passage is reduced.

An additional important advantage of the third preferred embodiment of FIGS. 7, 8 and 9 relates to the chamber 24". In use, a syringe is used to fill the interior volume of the deflated balloon, the support structure, the chamber 24", and the tube 13", and then the cap 11" is used to seal the tube 13". Then, when it is desired to inflate the balloon, finger pressure is applied directly to the chamber 24" by pressing the chamber 24" between the thumb and an opposed finger of the user.

The use of the chamber 24" instead of a syringe to inflate the balloon provides several important advantages. First, the chamber 24" allows the user to control the inflation pressure precisely and directly, much more precisely than is possible when a syringe is used to inflate the balloon. In this way the chance of over-inflation of the balloon is reduced. Preferably the volume of the chamber 24" is small enough that the free balloon cannot be burst by finger pressure on the chamber 24".

Second, the chamber 24" provides the user with a direct, tactile information as to the fluid pressure in the balloon. This information allows the user to directly feel when balloon pressure increases as the balloon is pulled through a body passage. The user can quickly and instinctively react to excessive pressure by relaxing the pressure he applies with his fingers to the chamber 24", thereby reducing balloon pressure. In this way the ever present danger of applying damaging forces to the body passage is further reduced.

The solder bond 40 is placed adjacent the proximal end of the balloon 50 in order to isolate the bonding region 54 from this elongation of the coil spring 32. This improves the reliability and increases the life of the bonding region 54.

The balloon catheter 10 of these preferred embodiments provides a number of significant advantages. Because the sheath 42 is formed of silicone rubber it is soft and flexible. The coil spring 32 provides memory allowing the catheter to assume its original configuration after storage and use, and the silicone rubber sheath 42 does not soften at body temperature.

Furthermore, silicone rubber is relatively inert, and because of the coil spring 32 the entire catheter is radiopaque. The smooth molded tip section 52 can be used either for embolectomy or thrombectomy procedures. Furthermore, in that the balloon 50 is formed of silicone rubber, it is softer and more conformable than latex rubber balloons of the prior art. These features of the balloon 50 allow it to assume the contour of the body passage at lower contact pressures. Therefore, reduced contact pressures are required to conform the balloon to the body passage and lower pressure is transmitted to the body passage wall. Furthermore, because of the softness and compliancy of the balloon 50, it will extend longitudinally and assume a somewhat pear shape configuration when excessive withdrawal forces are applied. This further reduces balloon contact area and significantly reduces the shear stress on the passage wall. This longitudinal extension further limits radial pressure of the balloon on the body passage, reducing the possibility of rupturing or otherwise severely damaging the body passage. Because the balloon is directly bonded to the catheter and becomes an integral part of the catheter, there are no ties that can become separated from the catheter and lost. Furthermore, silicone rubber tends not to fragment if ruptured and therefore there is a reduced danger of silicone fragments becoming lost within the body passage.

The coil spring 32 provides longitudinal rigidity and radial support to the catheter. As described above, its extensibility also provides a tactile signal to the user as well as a reduction in the stretching forces applied to the balloon and a reduction in the volume of the balloon when necessary. The catheter can be packaged in a coiled position and placed within a small package for storage. No special conditions are necessary for storage, and if the catheter is taken out of its sterile package but not used it can be resterilized using steam or ethylene oxide gas.

Of course, it will be apparent to those skilled in the art that various changes and modifications to the preferred embodiment described above can be made without departing from the spirit and scope of the present invention. For example, in some embodiments it may be advantageous to extrude the silicone rubber sheath over the coil spring to fabricate the support structure. In addition, other elongatable support structures can be used to provide the tactile signal of excessive stretching force, and other types of means for receiving and storing fluid from the balloon when fluid pressure within the balloon exceeds a predetermined value can be used.

Other resilient materials in addition to silicone rubber, such as low durometer urethane or latex, for example, can be used in some embodiments. These and other changes and modifications can be made without departing from the true spirit and scope of the present invention. It is therefore intended that all such changes and modifications be covered by the following claims.

We claim:
1. An embolectomy catheter for insertion in a vascular passage, said catheter adapted to be pulled through said vascular passage to remove material therefrom, said catheter comprising:
   an inflatable balloon sized to fit within the body passage;
   an elongated support member having a diameter sized to fit within the body passage; and
   means for securely mounting the balloon to the support member;
   said support member having means included therein for permitting the support member to perceptibly elongate in response to an applied stretching force greater than a first value while exhibiting substantially no perceptible elongation in response to an applied stretching force less than a second value, no greater than the first value, said second value chosen to allow the catheter to be pulled through the vascular passage without perceptibly elongating the support member such that the support member does not perceptibly elongate in use when safe stretching forces are applied to the support member in pulling the balloon through the vascular passage, said first value chosen such that the support member perceptibly elongates when an excessive stretching force is applied to the support member in pulling the balloon through the vascular passage, thereby providing a tactile indication to a user that an excessive force is being applied.

2. The catheter of claim 1 wherein the second value is about one-half pound.

3. The catheter of claim 1 further including means for isolating the balloon from the elongation of the support member.

4. The catheter of claim 1 wherein the support member defines a lumen in fluid communication with the balloon, and the volume of the lumen increases when the support member elongates such that elongation of the support member causes a reduction in the volume of the balloon to reduce pressure exerted on the vascular passage by the balloon.

5. The catheter of claim 1 further comprising:
a chamber in fluid communication with the balloon, said chamber secured to the support member at a point remote from the balloon and having at least one, flexible, deformable wall adapted to be directly manipulated by digital pressure of a user to provide precise and direct control of the inflation pressure of the balloon during the application of stretching forces to the support member in pulling the balloon through the vascular passage.

6. The catheter of claim 5 wherein the flexible wall comprises an elastomeric material which is substantially inextensible under digital pressure of a user, and the chamber is sized to fit between the thumb and an opposed finger of the user.

7. An embolectomy catheter for insertion in a vascular passage, said catheter adapted to be pulled through said vascular passage to remove material therefrom, said catheter comprising:
an elongatable coil spring having a diameter sized to fit within the vascular passage;
an elongatable sheath disposed around at least a portion of the coil spring;
a balloon;
means for connecting the sheath to the balloon in a fluid tight manner such that the balloon is in fluid communication with the interior of the coil spring and fluid can be passed through the interior of the coil spring to the balloon to inflate the balloon;
said coil spring and said sheath cooperating to form a support member for the balloon, said coil spring configured such that the support member exhibits substantially no perceptible elongation in response to an applied stretching force less than a first value sufficient to pull the balloon through the body passage, yet elongates perceptibly when an excessive stretching force greater than a second value is applied to the support member in pulling the balloon through the vascular passage, thereby providing a tactile indication to a user than an excessive force is being applied.

8. The catheter of claim 7 wherein the coil spring prevents the inner diameter of the sheath from decreasing excessively when the support member is elongated, such that the interior volume of the support member is greater when the support member is elongated than when the support member is in its rest condition and the volume of the balloon is reduced when the support member is elongated, thereby reducing the pressure applied by the balloon to the vascular passage when the support member is elongated.

9. The catheter of claim 7 further including means for isolating the balloon from the elongation of the support member.

10. The catheter of claim 9 wherein the isolating means includes means for bonding together a plurality of coils of the coil spring in a region of the coil spring adjacent the balloon.

11. The catheter of claim 10 wherein the bonding means includes a soldered joint.

12. The catheter of claim 7 further comprising:
a chamber in fluid communication with the balloon, said chamber secured to the support member at a point remote from the balloon and having at least one flexible, deformable wall adapted to be directly manipulated by digital pressure of a user to provide precise and direct control of the inflation pressure of the balloon during the application of stretching forces to the support member in pulling the balloon through the vascular passage.

13. The balloon catheter of claim 12 wherein the chamber is shaped as a flattened disc sized to fit between the thumb and an opposing finger of the user.

14. The catheter of claim 7 wherein the first value is about one-half pound.

15. An embolectomy catheter for insertion in a vascular passage, said catheter adapted to be pulled through said vascular passage to remove material therefrom, said catheter comprising:
an elongated support member having a diameter sized to fit within the body passage and a distal end, said support member including an elongated coil spring and an extensible tubular sheath disposed around the coil spring;
a strain relief collar having a first end securely affixed to the distal end of the support member and a second end, said strain relief collar movable between a rest position and an extended position; and
a balloon having an end securely affixed to the strain relief collar;
said balloon having a lower inflation pressure than the strain relief collar such that for inflation pressures less than a first value the balloon inflates but the strain relief collar remains in its rest position, and that for inflation pressures greater than a second value, no less than the first value, the strain relief collar moves to its extended position in orer to receive fluid from the balloon to increase the length and reduce the diameter of the balloon.

16. The catheter of claim 15 wherein the balloon is a sleeve having an open end, and the open end is affixed to the strain relief collar.

17. The catheter of claim 16 wherein the strain relief collar is bonded to the open end of the balloon.

18. A balloon catheter for insertion in a body passage, said catheter comprising:
an elongated coil spring defining a lumen; a balloon tip mounted on one end of the coil spring, said tip having a terminal end section disposed over the distal end of the spring and an open end;
a strain relief collar affixed to the open end of the balloon tip such that the collar extends around a portion of the spring; and
an extensible sheath affixed to the strain relief collar and extending around a portion of the spring proximal to the strain relief collar;
said balloon tip, strain relief collar, and sheath forming a fluid tight unit such that pressurized fluid introduced into the sheath inflates the balloon tip;
the strain relief collar movable between a rest position, in which the collar is positioned against the spring, and an extended position, in which the collar extends away from the spring to receive fluid from the balloon to reduce fluid pressure within the balloon when the fluid pressure exceeds a first value;

the spring and sheath forming in combination a support member which perceptibly elongates when an excessive stretching force is applied to the support member in pulling the balloon through the body passage, thereby providing a tactile indication to a user that an excessive force is being applied.

19. The balloon catheter of claim 18 wherein a plurality of coils of the spring adjacent the strain relief collar are bonded together to prevent relative elongation thereof.

20. The balloon catheter of claim 19 wherein the plurality of coils are bonded together by solder.

21. The balloon catheter of claim 18 wherein the balloon tip is bonded to the collar and the collar is bonded to the sheath.

22. The balloon catheter of claim 18 wherein the balloon tip comprises a tip section and a balloon section bonded to the tip section.

23. A method for pulling an embolectomy catheter through a vascular passage comprising the following steps:

providing a catheter comprising:

an inflatable balloon sized to fit within the vascular passage;

an elongated support member having a diameter sized to fit within the vascular passage;

means for securely mounting the balloon to the support member near one end of the support member, and a balloon inflation structure mounted to the support member near the other end of the support member, said inflation structure including a chamber in fluid communication with the balloon, said chamber having at least one flexible, deformable wall adapted to be directly manipulated by digital pressure of a user to provide precise and direct control of the inflation pressure of the balloon;

inserting the catheter in a vascular passage; and continuously manipulating the at least one deformable wall with direct digital pressure to inflate the balloon as the catheter is withdrawn from the vascular passage in order to obtain a continuous tactile indication of and continuous, direct control over the inflation pressure of the balloon as the catheter is withdrawn from the vascular passage.

24. The method of claim 23 wherein the wall of the chamber is formed of an elastomeric material and is substantially inextensible by digital pressure of a user.

25. The method of claim 23 wherein the chamber is shaped as a flattened disc sized to fit between the thumb and an opposing finger of a user.

* * * * *